United States Patent [19]

Degelaen et al.

[11] Patent Number: 5,246,830
[45] Date of Patent: Sep. 21, 1993

[54] ENZYMATIC PROCESS FOR THE DETERMINATION OF β-LACTAM ANTIBIOTICS

[75] Inventors: Jacques Degelaen, Genappe; Jean-Marie Frere, Nandrin, all of Belgium

[73] Assignee: Ucb Bioproducts, S.A., Bruxelles, Belgium

[21] Appl. No.: 692,355

[22] Filed: Apr. 26, 1991

[30] Foreign Application Priority Data

Apr. 30, 1990 [GB] United Kingdom ............... 9009692

[51] Int. Cl.$^5$ .................... C12Q 1/00; C12N 1/00
[52] U.S. Cl. ..................... 435/4; 435/23; 435/24; 435/29; 435/184; 435/810; 435/825; 435/975; 436/23; 436/815
[58] Field of Search .............. 435/4, 23, 24, 29, 184, 435/810, 825, 975; 436/23, 815

[56] References Cited

U.S. PATENT DOCUMENTS

| | | | |
|---|---|---|---|
| 2,824,863 | 2/1958 | Schwtzer | 260/112 |
| 4,166,825 | 9/1979 | Plattner et al. | 560/34 |
| 4,546,076 | 10/1985 | Degalaen et al. | 435/24 |
| 4,686,182 | 8/1987 | Drake | 435/24 |
| 4,806,478 | 2/1989 | Stahl | 435/23 |

FOREIGN PATENT DOCUMENTS 0186944 7/1986 European Pat. Off. .

OTHER PUBLICATIONS

Frere et al., *Antimicrobial Agents and Chemotherapy*, vol. 18, No. 4, pp. 506-510, 1980.
Jamin et al, *Biochem J.*, vol. 280, pp. 499-506, 1991.
Schindler et al., *The Journal of Antibiotics*, vol. 39, No. 1, pp. 53-57, Jan. 1986.
Adam et al, *Biochem J.*, vol. 270, pp. 525-529, 1990.
Lowe et al., *Chemical Abstracts*, vol. 63, No. 3 (1965), Abstract No. 3243e.

Primary Examiner—Michael G. Wityshyn
Assistant Examiner—Abdel A. Mohamed
Attorney, Agent, or Firm—Wenderoth, Lind & Ponack

[57] ABSTRACT

An enzymatic process for the determination of β-lactam antibiotics in a biological liquid, comprising the steps of (1) incubating the liquid with soluble D-alanyl-D-alanine-carboxypeptidase produce by Actinomadura R39, the β-lactam antibiotic reacting with the enzyme to form an inactive and equimolecular enzyme-antibiotic complex; (2) incubating the mixture obtained with a solution of a thioester substrate having the formula $$R_1-R_2-S-CH-COOH$$
$$|$$
$$R_3$$

wherein
$R_1$ = benzoyl, phenylacetyl or $N^\alpha$-acetyl-L-lysyl,
$R_2$ = glycyl or D-alanyl, and
$R_3$ = hydrogen or methyl
so as to form, by hydrolysis, a 2-mercaptoalkanoic acid having the formula $$HS-CH-COOH$$
$$|$$
$$R_3$$

in an amount proportional to the residual enzymatic activity, said incubation being further conducted in the presence of glycine or of a D-amino acid; (3) determining the amount of 2-mercaptoalkanoic acid formed, and (4) comparing the determination of step (3) with a standard, to obtain the antibiotic concentration in the biological liquid.

A test set for carrying out this process is also disclosed.

18 Claims, No Drawings

ENZYMATIC PROCESS FOR THE DETERMINATION OF β-LACTAM ANTIBIOTICS

The present invention relates to a novel, fast and sensitive enzymatic process for the determination of β-lactam antibiotics in a biological liquid. It also relates to a test set which can be used for carrying out this process.

Nowadays, antibiotics are very widely used not only as therapeutic agents in the treatment of infectious diseases caused by bacteria, but also as food preservatives and as growth-stimulating additives to animal feed. There is, therefore, an ever-increasing need to be able to detect the presence of antibiotics, even in very low concentrations, in complex biological liquids such as milk, urine, blood, serum, saliva, meat extracts, fermentation liquids or buffered aqueous media.

The case of milk production is an example of this. Indeed, it is well known to use penicillins to treat certain infectious diseases of dairy cattle, e.g. mastitis. However, for obvious medical reasons, milk intended for human consumption must in principle be free from any trace of antibiotics. On the other hand, penicillin concentrations of 0.005 I.U./ml or less can have harmful effects during the manufacture of milk-based products such as cheese or yogurt. Furthermore in certain countries, the concentration of antibiotic allowed by law must not exceed 0.004 I.U./ml.

It is therefore necessary to be able to determine, quickly and accurately, the concentration of penicillins in milk produced by cattle and, preferably, to be able to do this directly on site at the farm.

Microbiological processes enabling the determination of relatively low concentrations of β-lactam antibiotics in biological liquids have existed for a long time. These processes involve observing the degree to which the growth of micro-organisms sensitive to antibiotics is inhibited in the presence of a sample of the biological liquid. However, these processes are time-consuming and require a high level of technical skill; in the best case, it can take about 2 to 3 hours for a result to be obtained, which is not admissible in practice.

More recently, fast microbiological process has been proposed for detecting the presence of antibiotics in a biological liquid, more particularly milk (see U.S. Pat. No. 4,239,852).

According to this method, the liquid sample to be examined is incubated on the one hand, together with cells or cell parts of a micro-organism which is very sensitive to antibiotics, more particularly *Bacillus stearothermiphilus*, and on the other hand, with an antibiotic tagged with a radioactive element or with an enzyme. During incubation, the antibiotic, if present in the sample, competes with the tagged antibiotic for binding to the receptor sites on the cells or cell parts. Afterwards the amount of tagged antibiotic which has become attached to the cells or cell parts is determined. This provides an indication of the presence (or absence) of antibiotics, since the amount of tagged antibiotic attached is inversely proportional to the concentration of antibiotic in the sample.

According to the author of this U.S. patent, this process can detect antibiotic concentrations as low as 0.01 I.U./ml or even as 0.001 I.U./ml in milk, in slightly less than 15 minutes.

The major drawback of this process, however, is that to obtain this result it is compulsory to use an antibiotic tagged with a radioactive element ($^{14}C$ or $^{125}I$), the amount of which has to be determined with the aid of a special apparatus such as for example a scintillation counter. Furthermore, it is not totally without danger for the person carrying out the analysis to handle such radioactive materials, even in very small amounts.

Admittedly, Example 2 of this U.S. Patent Specification describes another embodiment of this process in which an enzyme-tagged antibiotic is used and in which the amount of tagged antibiotic is determined by a visual colorimetric method. However, this variant can detect only whether there is more (or less) than 0.05 IU/ml of penicillin in a sample of milk. This process is, therefore, considerably less sensitive and consequently much less useful.

There are also commercial tests based on the use of monoclonal or polyclonal antibodies. Indeed, as is known, tests can be prepared on the basis of conventional techniques of immunological diagnosis (ELISA, agglutination with latex, radio-immunological methods and the like). As an example of this kind of test the SPOT TEST can be mentioned, which is marketed by ANGENICS (USA).

The disadvantages of this kind of test are that they are generally very complex and above all that they can only be used to detect a very limited number of antibiotics. This latter disadvantages results from the high specificity of the antibodies; they can recognize only antibiotics which are structurally similar to the one chosen for immunization. This is particularly delicate in the case of the β-lactam antibiotics.

There is also a known enzymatic process for the determination of low concentrations of β-lactam antibiotics in human serum and in milk (J-M. FRERE et al., Antimicrobial Agents and Chemotherapy 18, (1980, No. 4), 506–510).

This process (hereinafter designated as "the J-M FRERE process") is more interesting, since it does not necessitate the use of radioactive materials requiring sophisticated measuring apparatus, and at the same time it is also very fast and remarkably precise. This process is based on the use of a specific enzyme, i.e. the soluble exocellular D-alanyl-D-alanine-carboxypeptidase, which is produced by Actinomadura R39 (previously called Streptomyces R39). In the present specification, this enzyme will be designated as "enzyme R39". This enzyme possesses a specific activity for hydrolyzing the D-Alanyl-D-alanine end groups of various peptides with release of the terminal D-alanine.

Another important characteristic of enzyme R39 is that it reacts with β-lactam antibiotics, to form very rapidly an inactive, substantially irreversible equimolecular enzyme-antibiotic complex.

In the J-M FRERE process, these properties of enzyme R39 are used to determine very low concentrations of β-lactam antibiotics. The method comprises three essential steps.

In the first step, a definite volume of a sample of the liquid to be examined is incubated with a definite amount of enzyme R39. The incubation is conducted under conditions allowing the β-lactam antibiotic, if present in the sample, to react with the enzyme to form an inactive, substantially irreversible equimolecular enzyme-antibiotic complex.

In the second step, a definite amount of substrate, e.g. $N^\alpha$, $N^\epsilon$-diacetyl-L-lysyl-D-alanyl-D-alanine, is incubated with the product obtained in the first step, under conditions allowing the substrate to be hydrolyzed by the enzyme, to form an amount of D-alanine corresponding to the residual enzymatic activity of the enzyme R39 which has not been complexed with the antibiotic in the first step.

In the third step, the amount of D-alanine thus formed is determined. Those skilled in the art will easily understand that the amount of D-alanine formed in the second step depends on the residual activity of the enzyme and is therefore inversely proportional to the amount of antibiotic present in the sample.

In the J-M FRERE process, the amount of D-alanine is determined by an enzymatic method. This is based on two coupled enzymatic reactions. In the first reaction, D-alanine is oxidized to pyruvic acid with the aid of a D-amino acid oxidase (in the presence of its co-enzyme, flavin-adeninedinucleotide); simultaneously a corresponding amount of hydrogen peroxide from atmospheric oxygen is formed. In the second reaction, the hydrogen peroxide formed is used to oxidize o-dianisidine with the aid of a peroxidase. A brown coloration is produced, the intensity of which depends on the amount of D-alanine.

This, therefore, makes it possible to determine the amount of D-alanine by a colorimetric method, either visually or by measuring the optical density with a spectrophotometer ($\lambda max = 460$ nm).

It is thus possible, by preparing a series of samples with a known antibiotic concentration and by applying this process, to plot a standard curve which relates the percentage residual enzymatic activity of enzyme R39 to the antibiotic concentration.

In order to obtain a quantitative indication of the antibiotic concentration in a sample, exactly the same procedure is carried out and the antibiotic concentration is determined referring to this standard curve.

Of course, this quantitative evaluation requires use of a spectrophotometer.

However, there is no need for a spectrophotometer or similar measuring apparatus in order to determine whether or not the antibiotic concentration exceeds a certain critical value.

It suffices to know beforehand the critical antibiotic concentration at which the activity of the enzyme R39 is totally suppressed or, in other words, the antibiotic concentration at which no D-alanine is formed and consequently no coloration occurs. Knowing this critical concentration, it is obvious that it is possible, by a simple visual inspection of the result of the determination, to judge whether or not a given sample contains an antibiotic concentration which is lower or higher than the said critical concentration. It is, therefore, apparent that by using this process an indication of the antibiotic concentration in milk can quickly and accurately be obtained, without the use of a special instrument.

Furthermore, this process makes it possible to determine relatively low concentrations of $\beta$-lactam antibiotic in milk and in human serum. Thus for example, it is possible, starting from milk samples of about 20 $\mu$l in volume and incubating them with 3 picomoles of enzyme R39, to quantitatively determine (using a spectrophotometer) concentrations of penicillin as low as 0.02 I.U./ml of milk, whereas concentrations of more than 0.09 I.U./ml of milk can be qualitatively determined by the visual method described above, in less than one hour.

However, the J-M. FRERE process has several serious drawbacks. First, the sensitivity of the J-M. FRERE process is insufficient, particularly in the case of biological liquids (milk, saliva, serum and the like). It is true that this sensitivity could be increased either by reducing the amount of enzyme R39 used, but this would increase the reaction time in both the first and second steps of the process, or by increasing the volume of the sample which must be incubated with enzyme R39, and in that case the reaction time in the first step of the process should be increased. Unfortunately, the sensitivity of the J-M. FRERE process cannot be increased in this way, particularly not in the case of complex liquids of biological origin. Indeed, it has been found that a proper determination cannot be realized when the volume of the sample of biological liquid exceeds a certain critical value, which varies with the nature of the biological liquid. Thus, in the case of milk and serum, when the sample volume for incubation exceeds about 50 $\mu$l, it is found that the amount of oxidized o-dianisidine formed, is greatly reduced. Finally, in the case of urine, no enzymatic activity at all is detected, even when using sample volumes as low as 10 $\mu$l. It is, therefore, impossible to use this process for determining antibiotics in urine.

It is assumed that biological liquids contain substances which inhibit the action of the enzymes used in the J-M. FRERE process. Thus, in practice, this means that large sample volumes can only be used in the best circumstances at the expense of increased amounts of reactancts at least proportional to the increase of the volume. This is clearly undesirable in view of the high costs of the enzymes used, particularly D-amino acid oxidase and its co-factor, flavin-adenine-dinucleotide.

An improved version of the J-M. FRERE process is marketed in the form of a test bearing the trade-mark "Penzym". This test is used mainly as screening test for milk arriving at dairies.

The test is carried out in two steps. In the first step, 50 $\mu$l of milk are incubated with 1.5 picomole of enzyme R39 for 5 minutes at 47° C. Next, in the second step, all the reagents for determining the residual enzymatic activity, i.e. the substrate $N^\alpha$, $N^\epsilon$-diacetyl-L-lysyl-D-alanyl-D-alanine, the D-amino acid oxidase, the flavin-adenine-dinucleotide, the peroxidase and the chromogenic reagent, are added to the incubation medium and the whole is incubated for 15 minutes at 47° C. At the end of the incubation, by comparison with a color chart, a yellow color devoid of pink indicates the presence of $\beta$-lactam antibiotics at a concentration higher than 0.017 I.U./ml of milk. On the other hand, the presence of a pink color indicates either the absence of antibiotics (an intense pink color) or the presence of antibiotics at concentrations up to 0.017 I.U./ml, the intensity of the obtained pink color being inversely proportional to the antibiotic concentration.

Thanks to this test antibiotic concentrations in milk as low as 0.017 I.U./ml can be visually determined in 20 minutes.

However, even this improved version of the J-M. FRERE process has sensitivity and rapidity characteristics which do not permit its use either in countries where the law allows only extremely low antibiotic concentrations, e.g. 0.004 I.U./ml, or as an ultra-rapid test for enabling the dairy farmer to carry out tests at the farm in less than 5 minutes.

The increase of the sensitivity and the reduction of the response time of the Penzym test are subject to the same constraints as already mentioned above with regard to the J-M. FRERE process. In addition, this test is made on very small sample volumes and therefore requires some experience in micro-assay techniques to be carred out properly.

To avoid all the problems connected with the use of a test carried out completely in the presence of the biological liquid, a proces has also been proposed in which the enzyme R39 is immobilized on a water-insoluble support, particularly on a poly(N,N-dimethylacrylamide) resin. This process is disclosed in U.S. Pat. No. 4,546,076, and comprises the following three steps:

(1) the enzyme immobilized on the support is incubated in the presence of the biological liquid;
(2) the immobilized enzyme is then separated from the biological liquid and washed;
(3) the residual activity of enzyme R39 is determined by a colorimetric determination of the D-alanine formed from the peptide substrate using a system of reagents comprising a D-amino acid oxidase and its co-factor, a peroxidase and a chromogenic reagent, the result being obtained either by a simple visual inspection or by means of a spectrophotometer.

This process has a number of advantages:

there is no longer any interference between the biological liquid and the enzymes used for determining D-alanine, since the biological liquid has already been removed at step (2) of the process;
excellent determinations can be made on larger sample volumes of up to 5 ml; and
the sensitivity is much greater, since the process can be used to determine visually concentrations of penicillin G of more than 0.002 I.U./ml of milk.

However, the process also has disadvantages:

as with all processes requiring a separation step, the reproducibility of the results is not as good as in a homogeneous-phase process;
whatever method of separation is used, the inevitable result is an increase in the duration and the complexity of the process;
even though this process allows a high sensitivity to be obtained by simple visual inspection, and which can go to 0.002 I.U. of penicillin G per ml, the time necessary for obtaining this result is clearly too long (at least 30 minutes) for this process to be used for rapid detection when milk is collected at the farm; and
moreover, the expense is much higher than the expense for a homogeneous-phase test.

It would represent a considerable technical and economic advance for the art to have at its disposal a process free from the various disadvantages of the prior art processes, particularly of the J-M. FRERE process or the processes derived therefrom, such as the "Penzym" test or the process described in U.S. Pat. No. 4,546,076.

In other words, an object of the present invention is to provide a process offering a combination of advantageous properties, because:

the result is provided very quickly, e.g. in 5 minutes or less;
the sensitivity is very high, enabling the process to be used even in countries where the law is very severe and requires that the antibiotic concentration in milk should not exceed 0.004 I.U./ml or less;
determinations can be carried out on large sample volumes of 1 ml or more, thus enabling the easy execution of the process by unskilled personnel;
the process is inexpensive and very simple in use.

These objects are achieved by the process of the present invention which distinguishes itself by the following essential characteristics:

(1) use of a special thioester-type substrate for enzymes R39, so as to form by hydrolysis a compound containing a free SH group, which can be determined by a simple, inexpensive colorimetric method, without the need for enzymes whose activity is distrubed by the components of the biological liquid;
(2) conducting the hydrolysis of the substrate by the enzyme in the presence of a D-amino acid or glycine, which substantially activates this hydrolysis.

The present invention therefore provides a novel enzymatic process for the determination of β-lactam antibiotics in a biological liquid, which process comprises the steps of:

(1) incubating the biological liquid with the soluble D-alanyl-D-alanine carboxypeptidase produced by Actinomadura R39, said incubation being conducted under conditions allowing the β-lactam antibiotic, if present in the said liquid, to react with the enzyme to form an inactive and substantially irreversible equimolecular enzyme-antibiotic complex;
(2) incubating the mixture obtained at the end of step (1) with a substrate solution under conditions allowing the substrate to be hydrolyzed by the enzyme, said substrate being a thioester having the general formula

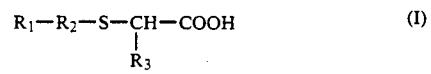

wherein
$R_1$ represents a benzoyl, phenylacetyl or $N^\alpha$-acetyl-L-lysyl radical,
$R_2$ represents a glycyl or D-alanyl radical, and
$R_3$ is a hydrogen atom or a methyl radical,
which forms, by hydrolysis, a 2-mercaptoalkanoic acid having the formula

in which $R_3$ has the meaning given above,
in an amount proportional to the residual enzymatic activity, said incubation being further conducted in the presence of a D-amino acid or of glycine, which activates the hydrolysis of the substrate by the enzyme;
(3) determining the amount of 2-mercaptoalkanoic acid of formula II formed in step (2), and
(4) comparing the value determined in step (3) with a standard, to obtain the concentration of antibiotic in the biological liquid.

During our research work in this field, we have found that enzyme R39 has a specific hydrolysis activity on the thioester bonds of certain compounds having a terminal thioester group and, more particularly, has a hydrolysis activity on the thioesters having the general formula I mentioned above. This discovery is surprising in itself since, to the best of our knowledge, there is no example known in the prior art of a D-alanyl-D-alanine-carboxypeptidase which also acts as a thioesterase. We have taken advantage of this unexpected property of enzyme R39 to develop a new improved enzymatic process for the determination of β-lactam antibiotics in biological liquids.

Contrary to the J-M. FRERE process and the similar processes described hereinbefore, the substrate for enzyme R39 used according to the invention is a thioester having the general formula I, which forms, by hydrolysis, a 2-mercaptoalkanoic acid having the formula II given above. This novel substrate provides numerous advantages, both technological and economic. Indeed, the 2-mercaptoalkanoic acid of formula II, formed from this substrate (and the amount of which is proportional to the residual activity of enzyme R39) can be determined by a simple colorimetric method, which no longer requires enzymes such as D-amino acid oxidase and its co-enzyme. In addition to a substantial reduction of cost price, one of the main drawbacks of the J-M. FRERE process is thus overcome since there is no longer any possible interference between the components of the biological liquid and the reagents of the colorimetric determination, the latter being simple chemical reagents and not enzymes. Therefore, the process according to the present invention enables the determination to be carried out directly on the unprocessed biological liquid as such; it is no longer necessary for samples to be freed previously from any substances which could disturb the colorimetric determination.

Furthermore, since the determination of residual enzyme activity is no longer influenced by factors present in the biological liquids, it is also possible to work with samples of biological liquid having a volume up to 10 ml. The process according to the present invention can therefore be used on larger volumes and is thus even more easily carried out by unskilled persons.

Moreover, since it is possible to work on larger sample volumes, the process according to the present invention makes it possible to obtain a much higher sensitivity. As will be shown hereinafter in the examples, the process according to the present invention makes it possible to determine visually and easily amounts in the order of 0.004 I.U. of penicillin G per milliliter of milk in 15 minutes. It is even possible, referring to a color chart, to manage to detect concentrations as low as 0.002 I.U./ml.

Furthermore, we have found surprisingly that the addition of a D-amino acid or glycine considerably increases the rate of the hydrolysis reaction of the thioester-type substrate of formula I under the influence of the enzyme. Our research work in this field has shown that a number of D-amino acids as well as glycine can have an activating effect on the thioester hydrolysis reaction. Among the best activators, there can be mentioned, D-alanine, D-methionine, D-arginine, D-phenylalanine, D-serine, D-histidine, D-valine, D-tryptophan and D-2-aminobutyric acid.

Thus for example, if the activity of enzyme R39 is expressed in units per milligram of enzyme (one unit of enzyme hydrolyzes 1 micromole of substrate per minute at 47° C.), it has been found that the activity of enzyme R39, using [(N-benzoyl-D-alanyl)thio]-acetic acid as substrate, is equal to 8 units in the absence of D-alanine and 320 units in the presence of D-alanine. In other words, in the presence of this activator, the rate of hydrolysis of the substrate by enzyme R39 is 40 times higher. On the other hand, it has also been found that no amino acid having the L-configuration is capable of activating the hydrolysis of the substrate.

Therefore, according to the present invention, it is essential that the hydrolysis of the thioester-type substrate in step (2) is carried out in the presence of a D-amino acid, which activates the hydrolysis of the substrate by enzyme R39. Indeed, this measure permits a saving of considerable time in carrying out the process.

In this manner, by means of the process according to the present invention, it is easy to determine a penicillin G concentration of 0.016 I.U. per milliliter of milk in 5 minutes. By comparison, the "Penzym" test requires about 15 minutes to obtain the same result. By contrast to the prior-art processes, therefore, the process according to the invention is particularly attractive, for rapid antibiotic detection when milk is collected at the farm, especially since it is simple to work and does not require sophisticated apparatus.

Moreover, we have also found that the process according to the present invention can be applied successfully for the determination of antibiotics not only in milk, but also in other biological liquids such as serum, urine, saliva, meat extracts, fermentation liquids, buffered aqueous solutions and the like.

The prime advantage of the process of the present invention, therefore, is that it can be used, either to detect concentrations of $\beta$-lactam antibiotics of the order of about 0.016 I.U./ml, in a very short time (5 minutes) or to detect very low concentrations of $\beta$-lactam antibiotics of the order of 0.004 I.U./ml or less, in a slightly longer time (15 minutes), without requiring a special analytical apparatus and without the need to have recourse to a complex technology requiring a separation process.

The antibiotics, the concentrations of which can be determined using the process according to the invention, belong to the group of antibiotics characterized by the presence of a $\beta$-lactam ring in their molecule, i.e. as a rule, all the penicillins and cephalosporins. Examples of penicillins which may be mentioned include benzyl penicillin (penicillin G), ampicillin, phenoxymethylpenicillin, carbenicillin, methicillin, oxacillin, cloxacillin and the like. By way of example of cephalosporins there may be mentioned cephalosporin C, cephaloglycin, cephalothin, cephalexin, cephapirin and the like. Particularly favorable results have been obtained with penicillin G.

In step (1) of the process according to the present invention, a definite volume of a sample of the biological liquid is incubated with a definite amount of enzyme R39.

As explained above, it is possible to work with very large sample volumes. For a given amount of enzyme R39, by increasing the volume of the sample, the sensitivity of the process increases in parallel. For example, by doubling the volume of the sample the sensitivity is doubled, by tripling the volume of the sample, the sensitivity is tripled and so on. The volume of the sample can therefore be chosen to provide the desired sensitivity. In the case of milk, for example, the sensitivity of the process can be adapted to the standards laid down by the law of the country where it is used, or to the requirements of the dairy industry.

The same effect for a given volume of biological liquid can be obtained by reducing the amount of enzyme R39 (as in example 2 hereinafter). In this case, however, not only the duration of step (1) but also the duration of step (2) of the process must be increased proportionally.

In practice, the choice of the amounts of enzyme R39 and of biological liquid to be used, will depend, on the one hand, on the way the process is carried out and, on the other hand, on the desired sensitivity or speed.

Thus, for example, if the process according to the invention is used for determining the contamination of milk on the farm, it is preferred to work with large sample volumes for easier manipulation. Volumes between 1 and 10 ml are preferred. If the process is carried out in a laboratory with micro-assay equipment, sample volumes of between 50 µl and 1 ml will be perfectly suitable.

Moreover, the choice of the amounts of enzyme and biological liquid used will depend essentially on the required sensitivity. Thus, for example, in the laboratory, where small volumes can be used and where a sensitivity of 0.01 I.U./ml is required, the chosen amount of enzyme will be about 1 picomole and the volume of biological liquid will be about 50 µl. To obtain a sensitivity of 0.005 and 0.0025 I.U./ml respectively, the volume of biological liquid will be increased to 100 µl and 200 µl respectively, without changing the amount of enzyme.

The excellent sensitivity, the rapidity and accuracy of the process according to the invention result from the particular characteristics of enzyme R39, on the one hand, and from the process used for the determination of the residual activity of enzyme R39, on the other hand.

In fact, enzyme R39, is characterized by:
the extremely rapid formation of an inactive equimolecular enzyme-antibiotic complex;
the extraordinary stability of the said complex, because, once formed it only breaks down very slowly. By way of example, the half-life of the complex formed between enzyme R39 and penicillin G is about 70 hours at 37° C.; and
an excellent enzymatic activity, shown by very rapid hydrolysis of the terminal group of the thioester-type substrate of formula I, under the influence of a specific activator.

Thanks to these three characteristics, enzyme R39 occupies a privileged position compared with the other D-alanyl-D-alanine carboxypeptidases identified hitherto. Indeed, since the time of break down of the enzyme-antibiotic complex is infinitely greater than the total time required, respectively, for forming the complex and for measuring the residual enzymatic activity, there is no danger that the results of the determination will be vitiated by the release of free active enzyme due to premature break down of the enzyme-antibiotic complex.

When the D-alanyl-D-alanine carboxypeptidase known today are evaluated, apart from enzyme R39, none of them meets these conditions perfectly. Indeed, either the rate of formation of the complex is some ten times slower, or the stability of the enzyme-antibiotic complex is completely insufficient, or the rate of hydrolysis of the substrate is much too slow (this is the case, inter alia, with all membrane-bound endocellular carboxypeptidases). Enzyme R39 is the specific, soluble exocellular D-alanyl-D-alanine carboxypeptidase which is excreted by Actinomadura R39, when this micro-organism (deposited on Jul. 10, 1981 at the Institut Pasteur in Paris, under accession number I-127) is cultivated in a suitable culture medium.

To carry out the process according to the invention, the enzyme must of course be substantially pure. Its preparation and purification can be carried out according to the methods described in the literature (in this connection, see the article by J-M. FRERE et al., Biochem. J. 143, (1974), 233-240, entitled "Molecular Weight, Amino Acid Composition and Physicochemical Properties of the Exocellular DD-Carboxypeptidase-Transpeptidase of Streptomyces R39"). However, this enzyme in pure form is at present commercially available; it can be obtained from UCB-BIO-PRODUCTS S. A. (Belgium).

Enzyme R39 possesses an excellent stability; it withstands high temperatures of up to 60° C. It is for this reason that the incubation of the biological liquid with enzyme R39 can be carried out without difficulty within a temperature range of from 20° to 50° C. The preferred incubation temperature is near 47° C. Indeed, under these conditions the incubation time, which is closely related to the time required to form the inactive equimolecular enzyme-antibiotic complex, is very short. An increase in the incubation temperature will have the effect of reducing the incubation time, and vice versa. It is, therefore, possible to shorten the duration of the process by increasing the temperature.

In step (2) of the process according to the present invention, the mixture obtained at the end of step (1) is incubated with a definite amount of the thioester-type substrate of formula I, in solution, in the presence of glycine or a D-amino acid, which activates hydrolysis of this substrate by the enzyme. During this step, the fraction of the enzyme which was not consumed in the formation of the enzyme-antibiotic complex in step (1) of the process is used to hydrolyze the thioester substrate of formula I. This hydrolysis reaction will produce an amount of 2-mercaptoalkanoic acid of formula II, which is proportional to the residual activity of enzyme R39.

The thioesters of formula I are new compounds, except for [(N-benzoylglycyl)thio]-acetic acid, which is known from U.S. Pat. No. 2,824,863.

The thioesters of formula I can be prepared by a conventional process, using reactions known per se. As a general rule an acid of formula III, previously activated, e.g. in the form of mixed anhydrides or in the form of active esters, is condensed in an inert solvent such as chloroform, dichloromethane, ethyl acetate or dimethylformamide, with a 2-mercaptoalkanoic acid of formula II, in accordance with the following equation:

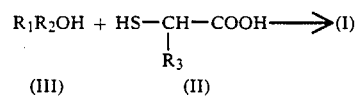

in which $R_1$, $R_2$ and $R_3$ have the same meanints as hereinbefore.

As examples of thioesters of formula I which can be used as a substrate, there can be mentioned, [(N-benzoyl-D-alanyl)thio]-acetic acid, 2-[(N-benzoyl-D-alanyl)thio]-propionic acid, [(N-phenylacetyl-D-alanyl)thio]-acetic acid, [(N$^\alpha$-acetyl-L-lysyl-D-alanyl)-thio]-acetic acid and the like. However, [(N-benzoyl-D-al;anyl)thio]-acetic acid gives the best results.

As non-limiting examples of D-amino acids which can be associated as activators with the substrates mentioned above, mention may be made of D-alanine, D-methionine, D-arginine, D-phenylalanine, D-serine, D-histidine, D-valine, D-tryptophan and D-2-aminobutyric acid.

According to a particularly preferred embodiment of the invention, D-alanine is associated with [(N-benzoyl-D-alanyl)thio]-acetic acid, uses as the substrate.

The amounts of substrate and activator required are not critical, provided that the process is conducted under conditions of enzyme saturation by the substrate.

The operating conditions to be observed during step (2) are substantially the same as those stated above for step (1). Incubation can be carried out within a temperature range of from 20° to 50° C., preferably at a temperature near 47° C. The incubation time with the non-inactivated fraction of enzyme R39 must be at least sufficient to form a measurable amount of 2-mercaptoalkanoic acid of formula II. At an incubation temperature of 47° C., this time can vary between a few seconds and 10 minutes depending on the amount of enzyme present and the volume of the sample. This time can be reduced by increasing the incubation temperature, or conversely, increased by reducing the incubation temperature. It is, therefore, also advantageous to increase the temperature of this incubation in all cases where the rapidity of the determination is an important factor.

In order to maintain optimum enzymatic activity, the incubation medium should preferably have a pH value of from 7 to 8.5. Usually the pH is maintained at about 8.0, by carrying out the incubation in a suitable buffer.

In step (3) of the process according to the present invention, the amount of 2-mercaptoalkanoic acid of formula II formed in step (2) is determined.

The determination of the 2-mercaptoalkanoic acid of formula II can be carried out by any known method, provided only that the method is fast, inexpensive and is specific for the 2-mercaptoalkanoic acid of formula II to the exclusion of all the other products which are present in the liquid to be examined.

For this reason, the preferred method is colorimetric determination with a reagent which produces a coloration by reaction with the free SH group of the 2-mercaptoalkanoic acid.

The chromogenic reagent can be chosen from among the chemical reagents noramlly used for this kind of reaction, such as for example 5,5'-dithiobis(2-nitrobenzoic) acid, condensation products of 4,4'-dithiobis(-phenylamine) with benzaldehydes, a phenanthroline-$Fe^{+++}$ system and the like.

A preferred chromogenic reagent is 5,5'-dithiobis(2-nitrobenzoic) acid, also called Ellman reagent, which produces a yellow color based on 2-nitro-5-mercaptobenzoic acid, formed by an exchange reaction with the SH group of the 2-mercaptoalkanoic acid. The intensity of the color is thus directly a function of the amount of the 2-mercaptoalkanoic acid.

For some applications, however, it may be preferable to use the red color produced by the reaction between phenanthroline and free SH groups in the presence of $Fe^{+++}$ cations.

The amount of chromogenic reagent to be used will depend on the amount of 2-mercaptoalkanoic acid formed in the particular application. It is preferred that the operating conditions are such that the molar amount of chromogenic reagent is slightly in excess of the maximum molar amount of 2-mercaptoalkanoic acid which may be formed in step (2) of the method.

It will be noted that enzyme R39 must necessarily be present from the beginning of step (1) of the process. Likewise, the substrate and the activator must necessarily be present from the beginning of step (2). However, the activator may be added at the beginning of step (1), and also the chromogenic reagent can be added at the beginning either of the first or the second step, or only at the end of step (2). In a preferred embodiment, in step (1) of the process, the enzyme R39 solution together with the milk sample will be incubated in the presence of the activator, in step (2) the substrate and the chromogenic reagent will be added, and steps (2) and (3) are simultaneously carried out under substantially the same conditions as those indicated above for step (2).

In step (4) of the process, the value determined in step (3) is compared with a standard to obtain the concentration of antibiotic in the biological liquid.

The quantitative determination of the antibiotic concentration can be carried out by the following method.

Firstly, a series of samples of the biological liquid, each containing a known concentration of $\beta$-lactam antibiotic are prepared.

This series will contain in addition to a certain number of samples containing increasing antibiotic concentrations, two samples of biological liquid free from antibiotic.

Next, all these samples are treated in a strictly identical manner, following steps (1), (2) and (3) of the process according to the present invention. For one of the antibiotic-free samples however, the enzyme solution used in step (1) is replaced by an identical volume of water. In this particular case, therefore, the solution obtained at the end of step (3) contains all the reagents except for enzyme R39. Owing to the absence of the enzyme, no 2-mercaptoalkanoic acid will, therefore, be formed in step (2), and consequently the chromogenic reagent, i.e. for example 5,5'-dithiobis(2-nitrobenzoic) acid, will not give any coloration. This sample will hereinafter be called the "blank sample".

In contradistinction thereto, the other antibiotic-free sample will produce a pronounced yellow coloration. Indeed, since the sample does not contain antibiotic, enzyme R39 is not inactivated in step (1) and a maximum amount of 2-mercaptoalkanoic acid of formula II will form (corresponding to the total activity of the enzyme R39 used) and, consequently, there will be a maximum amount of 5-mercapto-2-nitrobenzoic acid, resulting in a pronounced yellow coloration. This sample will hereinafter be called the "control sample".

It will also be understood that when the samples contain a molar amount of antibiotic which is less than the molar amount of enzyme R39 used, only a fraction of this enzyme will be inactivated by the antibiotic in step (1); in these cases, therefore, the amount of 2-mercaptoalkanoic acid of formula II formed will correspond to the residual activity of the enzyme fraction which has not been inactivated by the antibiotic, and consequently there will also be a corresponding amount of 5-mercapto-2-nitrobenzoic acid. In these cases, a yellow coloration will also be produced, but its intensity will be less than that observed with the control sample.

Finally, when the samples contain a molar quantity of antibiotic equal to or greater than the molar quantity of enzyme R39 used, the enzyme will be completely inactivated by the antibiotic during step (1); thus no 2-mercaptoalkanoic acid of formula II will be formed and consequently the chromogenic reagent will remain unchanged. In these cases, therefore, a coloration identical to that observed with the blank sample will be obtained.

In order to obtain an accurate determination, the optical density of the colorations obtained respectively with all the samples, including the blank and the control samples, is measured with a spectrophotometer. Since a certain optical density value is also found for the blank sample, it is necessary to subtract this value from those found for the control sample and for the other samples respectively.

From the resulting optical density values, the percentage residual activity (of the enzyme R39) is calculated for each sample. This percentage is equal to the ratio, multiplied by 100, of the optical density value found for a given sample to the optical density value found for the control sample.

A graph should then be plotted, showing the concentrations of antibiotic on the abscissa and the percentage residual activity of enzyme R39 on the ordinate.

A straight line is obtained which intersects respectively the ordinate at a point corresponding to the control sample (100% of residual enzymatic activity) and the abscissa at a point corresponding to the sample containing an amount of antibiotic equal to the molar quantity of enzyme R39 used (0% of residual enzymatic activity).

The resulting graph constitutes a "standard curve" for determining an unknown concentration of β-lactam antibiotic in a sample of the biological liquid used to prepare the graph. To this end, the samples are treated in a strictly identical manner, following steps (1), (2) and (3) of the process according to the present invention; the optical density of the coloration obtained is measured with a spectrophotometer, the optical density value found for the blank sample is subtracted therefrom, the percentage residual enzymatic activity is calculated in the manner indicated above, and the antibiotic concentration of the sample is obtained by reference to the standard curve.

It is thus possible quantitatively to determine antibiotic concentrations as low as 0.002 I.U./ml in a biological liquid in 15 minutes.

However, in some cases, this process requires the biological liquid to be clarified so that a spectrophotometer can be used. In principle, therefore, it has to be performed in a laboratory. However, if it is intended solely to determine whether or not the concentration of antibiotic exceeds a certain threshold (for example, in the case of milk a maximum concentration imposed by legal standards) it is not necessary to use a spectrophotometer.

This method, however, requires some prior explanations.

As shown above, the standard curve intersects the abscissa at a point corresponding to a sample containing an amount of antibiotic equal to the molar quantity of enzyme R39 used. At this critical antibiotic concentration, the percentage residual enzymatic activity is zero, since at the end of step (3) of the process according to the present invention a white coloration identical to that of the blank sample is obtained.

Above this critical concentration, the coloration is also identical to that of the blank sample, since the percentage residual enzymatic activity is still zero. Conversely below this critical concentration a yellow coloration is obtained because there is still a certain percentage residual enzyme activity.

It is therefore possible simply on the basis of the coloration observed at the end of step (3) of the process, to determine directly whether or not the antibiotic concentration in a sample exceeds the said critical concentration.

Therefore, it suffices to known the said critical concentration in advance to be able to determine rapidly, without using a spectrophotometer, whether a sample contains a concentration of β-lactam antibiotic which does (or does not) exceed this critical concentration. For this purpose, this sample is treated in identical manner, following steps (1), (2), and (3) of the process according to the present invention, followed simply by observation of the coloration obtained; if the coloration corresponds to that of the blank sample, the concentration of antibiotic will be at least equal to the critical concentration. If, on the other hand, the coloration is yellow, the concentration of antibiotic will be below the critical concentration.

It is thus possible, visually and with certainty, to determine whether samples contain more or less than 0.004 I.U. of antibiotic per ml of biological liquid and to do this within 15 minutes time.

Moreover, it will be possible, by using a color chart showing the variation in the intensity of the resulting yellow coloration as a function of the antibiotic concentration, to semi-quantitatively determine intermediate concentrations between 0 I.U./ml and the critical concentration. For instance, in an application where the critical concentration is 0.004 I.U./ml, it will be possible, at least without special difficulty, to determine a concentration of 0.002 I.U./ml.

This process, with or without a color chart, is therefore perfectly suitable for examining a series of milk samples, even outside the laboratory, for example on site at the farm, by unskilled personnel.

The method according to the present invention for the quantitative and qualitative determination of the antibiotic concentration has now been explained in detail with reference more particularly to the color change produced by 5,5'-dithiobis(2-nitrobenzoic) acid. However, those skilled in the art will easily understand that if other chromogenic reagents are used in this process, only the color observed will be different.

A further object of the present invention is to provide a test set which can be used for carrying out the process according to the present invention, i.e. which can be used for the determination of a β-lactam antibiotic in a biological liquid.

The test set comprises, in particular:
(1) a definite amount of soluble D-alanyl-D-alanine-carboxypeptidase produced by Actinomadura R39 (enzyme R39);
(2) a definite amount of a substrate which is a thioester having the general formula

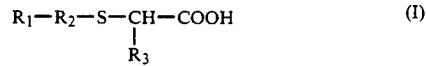

wherein
$R_1$ represents a benzoyl, phenylacetyl or $N^\alpha$-acetyl-L-lysyl radical,
$R_2$ represents glycyl or D-alanyl radical, and
$R_3$ is a hydrogen atom or a methyl radical,
(3) a definite amount of a D-amino acid or of glycine,
(4) a reagent allowing the determination of a 2-mercaptoalkanoic acid having the formula

in which $R_3$ has the meaning given above, and
(5) if appropriate, a standard with which the results of tests carried out with reagents (1), (2), (3) and (4) may be compared.

According to a preferred embodiment, the substrate is [(N-benzoyl-D-alanyl)thio]-acetic acid, the D-amino acid is D-alanine and reagent (4) is 5,5'-dithiobis(2-nitrobenzoic) acid.

According to a particularly preferred embodiment, the substrate and the reagent allowing the determination of 2-mercaptoalkanoic acid are combined in the form of a tablet in conjunction with the commonly used appropriate tableting excipients.

As the standard, a standard curve of the antibiotic concentration versus the percentage residual activity of the enzyme R39 can be included in the test set, if appropriate. It is thus possible to carry out quantitative determinations as explained above. However, this graph is not essential. Indeed, if the test set is to be used solely to determine whether the concentration of antibiotic exceeds or not a certain critical value, it suffices to indicate, in the directions for use, the concentration of antibiotic at which a change in the coloration is observed after the sample has been treated by the process according to the present invention.

The following Examples are given for the purpose of illustrating the present invention.

EXAMPLE 1

This example shows that the process according to the invention makes a very rapid determination of low concentrations of penicillin G in milk possible.

A series of 50 μl milk samples is prepared containing known concentrations of penicillin G, and two 50 μl milk samples free from penicillin G (blank and control).

1.5 picomole of enzyme R39, dissolved in 10 μl of 0.5M Hepes buffer (pH=8.0) containing 0.5M NaCl and 0.25M $MgCl_2$, and 20 μl of an aqueous solution containing 50 mg/ml of D-alanine are added to each sample (control sample+samples containing penicillin G). In the blank sample, enzyme R39 dissolved in Hepes buffer is replaced by 10 μl of 0.5M Hepes buffer (pH=8.0), containing 0.5M NaCl and 0.25M $MgCl_2$ (Hepes=4-hydroxyethyl-1-piperazineethanesulfonic acid). The mixture is incubated at 47° C. for 4 minutes.

Next, 5 μl of an aqueous solution containing 5 mg/ml [(N-benzoyl-D-alanyl)thio]-acetic acid and 10 μl of a phosphate buffer solution (pH=8.0; $KH_2PO_4+K_2HPO_4$) containing 2 mg/ml of 5,5'-dithiobis(2-nitrobenzoic) acid are added and the mixture is incubated at 47° C. for 1 minute.

The colorations obtained in the various samples are then observed.

The results obtained are reproduced in Table I.

TABLE I

| Sample | Penicillin G concentration (in I.U./ml) | Coloration |
|---|---|---|
| control | 0 | very intense yellow |
| 1 | 0.004 | intense yellow |
| 2 | 0.008 | medium yellow |
| 3 | 0.012 | pale yellow |
| 4 | 0.016 | white |
| 5 | 0.020 | white |
| 6 | 0.025 | white |
| blank | 0 | white |

As Table 1 shows, at a penicillin G concentration equal to or above 0.016 I.U./ml, a white color is obtained, similar to that obtained for the blank sample, whereas below this concentration a yellow coloration is produced, which increases in intensity as the penicillin G concentration decreases, to reach a very intense yellow coloration corresponding to a zero concentration of penicillin G (control sample).

It clearly appears that the process according to the invention makes it possible to determine visually whether a milk sample contains a penicillin G concentration of 0.016 I.U./ml or more, within 5 minutes. This makes the process particularly attractive for rapid screening of milk at the diary or on the farm.

EXAMPLE 2

This example shows that the process according to the invention is very sensitive.

The process is exactly the same as in Example 1 except that:

0.4 picomole of enzyme R39 (instead of 1.5 picomole) is added to the samples;

the first incubation lasts 10 minutes (instead of 4 minutes) and the second incubation lasts 5 minutes (instead of 1 minute).

The resultats obtained are reproduced in Table II.

TABLE II

| Sample | Penicillin G concentration (in I.U./ml) | Coloration |
|---|---|---|
| control | 0 | very intense yellow |
| 1 | 0.001 | intense yellow |
| 2 | 0.002 | medium yellow |
| 3 | 0.003 | pale yellow |
| 4 | 0.004 | white |
| 5 | 0.005 | white |
| 6 | 0.008 | white |
| 7 | 0.010 | white |
| blank | 0 | white |

This table shows that the process according to the invention can be used for visually detecting concentrations of penicillin G at least equal to 0.004 I.U. per ml of milk in 15 minutes. Moreover, it is also possible, by reference to a color chart, to detect even lower concentrations, such as 0.002 I.U./ml. Therefore, this process makes it possible to determine whether milk contains antibiotic concentration which exceeds (or not) the legal standards, even in countries where these standards are relatively severe.

EXAMPLE 3

This example shows that the process according to the present invention can be used to measure antibiotic concentrations in larger sample volumes.

The process is the same as in Example 1, except that:

the samples contain 3 ml of milk (instead of 50 μl);

24 picomoles (instead of 1.5 picomole) of enzyme R39 dissolved in 150 μl of 0.5M Hepes buffer (pH=8.0) and 600 μl of an aqueous solution containing 100 mg/ml of D-alanine are added to each sample;

the first incubation lasts 10 minutes (instead of 4 minutes);

120 μl (instead of 5 μl) of the aqueous solution of [(N-benzoyl-D-alanyl)thio]-acetic acid and 120 μl of a phosphate buffer solution (pH=8.0) containing 5 mg/ml of 5,5'-dithiobis(2-nitrobenzoic) acid are then added, and the second incubation lasts 5 minutes (instead of 1 minute).

The results obtained are given in Table III.

TABLE III

| Sample | Penicillin G concentration (in I.U./ml) | Coloration |
|---|---|---|
| control | 0 | very intense yellow |
| 1 | 0.002 | medium yellow |
| 2 | 0.003 | pale yellow |
| 3 | 0.004 | white |
| 4 | 0.006 | white |
| blank | 0 | white |

This table shows that the process according to the invention can be used for visually detecting the presence of 0.004 I.U. of penicillin G per ml of milk in large sample volumes (3 ml) in 15 minutes. It can therefore be carried out very easily by non-specialized persons.

The same results are obtained when the process according to the invention is used to measure concentrations of penicillin G in sample volumes of 1 ml of milk.

EXAMPLE 4

This example shows that the process according to the invention can be used with substrates other than [(N-benzoyl-D-alanyl)thio]-acetic acid.

The process is the same as in example 3, except that, after the first incubation, 120 µl of an aqueous solution containing 5 mg/ml of [(N-phenylacetyl-D-alanyl)thio]-acetic acid are added.

The results obtained are given in Table IV.

TABLE IV

| Sample | Penicillin G concentration (in I.U./ml) | Coloration |
|---|---|---|
| control | 0 | very intense yellow |
| 1 | 0.003 | pale yellow |
| 2 | 0.006 | white |
| blank | 0 | white |

This table shows that the process according to the invention can be carried out successfully using [(N-phenylacetyl-D-alanyl)thio]-acetic acid as a substrate.

EXAMPLE 5

This example shows that the process according to the invention can be carried out using various D-amino acids or glycine as activators for the hydrolysis of the substrate by the enzyme.

The process is the same as in example 3, except that the aqueous solution containing 100 mg/ml of D-alanine (test I) is respectively replaced by an aqueous solution containing 100 mg/ml of D-phenylalanine (test II), of D-serine (test III), of D-histidine (test IV), of D-methionine (test V), of D-2-aminobutyric acid (test VI), or by an aqueous solution containing 200 mg/ml of glycine (test VII).

The results obtained are given in Table V.

TABLE V

| Test | Sample | Penicillin G concentration (in I.U./ml) | Coloration |
|---|---|---|---|
|  | control | 0 |  |
| I |  |  | very intense yellow |
| II |  |  | very intense yellow |
| III |  |  | very intense yellow |
| IV |  |  | very intense yellow |
| V |  |  | very intense yellow |
| VI |  |  | very intense yellow |
| VII |  |  | very intense yellow |
|  | 1 | 0.003 |  |
| I |  |  | pale yellow |
| II |  |  | pale yellow |
| III |  |  | pale yellow |
| IV |  |  | pale yellow |
| V |  |  | pale yellow |
| VI |  |  | pale yellow |
| VII |  |  | pale yellow |
|  | 2 | 0.006 |  |
| I |  |  | white |
| II |  |  | white |
| III |  |  | white |
| IV |  |  | white |
| V |  |  | white |
| VI |  |  | white |
| VII |  |  | white |
|  | blank | 0 |  |
| I |  |  | white |
| II |  |  | white |
| III |  |  | white |
| IV |  |  | white |
| V |  |  | white |
| VI |  |  | white |
| VII |  |  | white |

This table shows that, in general, D-amino acids or glycine are suitable for carrying out the process according to the invention.

EXAMPLE 6

This example illustrates the application of the process according to the invention for the determination of cephapirin, an antibiotic of the cephalosporin group, in milk.

The process is the same as in example 3, but the samples of 3 ml of milk contain known concentrations of cephapirin.

The results obtained are reproduced in Table VI.

TABLE VI

| Sample | Cephapirin concentration (in µg/ml) | Coloration |
|---|---|---|
| control | 0 | very intense yellow |
| 1 | 0.002 | medium yellow |
| 2 | 0.003 | pale yellow |
| 3 | 0.004 | white |
| 4 | 0.006 | white |
| blank | 0 | white |

This table shows that the process according to the invention can be used for visually detecting the presence of 0.004 µg/ml of cephapirin in milk in 15 minutes time.

EXAMPLE 7

This example illustrates the application of the process according to the invention for the determination of low concentrations of penicillin G in serum.

The procedure of example 3 is followed, but the 3 ml milk samples are replaced by 3 ml serum samples containing known concentrations of penicillin G.

Moreover, after the second incubation lasting 5 minutes, the samples are centrifuged and the supernatants are diluted 10 times with water.

Then, the optical density is measured with a spectrophotometer at 410 nm.

The results obtained are given in Table VII.

The values of the optical density mentioned in Table VII are obtained by subtracting the optical density value found for the blank sample from the optical density values found respectively for the control sample and for the other samples.

TABLE VII

| Sample | Penicillin G concentration (in I.U./ml) | Optical density (at 410 nm) |
|---|---|---|
| control | 0 | 435 |
| 1 | 0.002 | 226 |
| 2 | 0.003 | 175 |
| 3 | 0.004 | 49 |
| 4 | 0.006 | 15 |
| blank | 0 | 0 |

This table shows that it is possible, by using a spectrophotometer, to determine quantitatively very low concentrations of penicillin G (as low as 0.002 I.U./ml) in a sample of serum.

EXAMPLE 8

In this example, the substrate and the reagent allowing the determination of 2-mercaptoalkanoic acid are combined in the form of a tablet.

The process is the same as in example 3. However, after the first incubation for a period of 10 minutes, a tablet is added which contains, 600 μg of [(N-benzoyl-D-alanyl)thio]-acetic acid and 600 μg of 5,5'-dithiobis(2-nitrobenzoic) acid.

This tablet has the following overall composition (in % by weight):

| | |
|---|---|
| substrate + reagent | 4% |
| polyethyleneglycol 6000 | 3% |
| Avicel* | 27% |
| starch | 10% |
| lactose | 55% |
| Aerosil** | 0.5% |
| magnesium stearate | 0.5% |

*microcrystalline cellulose
**colloidal silica

The results obtained are given in Table VIII.

TABLE VIII

| Sample | Penicillin G concentration (in l.U.ml) | Coloration |
|---|---|---|
| control | 0 | very intense yellow |
| 1 | 0.002 | medium yellow |
| 2 | 0.003 | pale yellow |
| 3 | 0.004 | white |
| 4 | 0.006 | white |
| blank | 0 | white |

This table shows that the process according to the present invention can be used when the substrate and the reagent allowing the determination of 2-mercaptoalkanoic acid, are combined in the form of a tablet; this offers a clear advantage both on a practical level and on the level of the stability of the reagents.

What is claimed is:

1. In an enzymatic process for the determination of a β-lactam antibiotic in a biological liquid comprising the steps of:
   (1) incubating a biological liquid with the soluble D-alanyl-D-alanine-carboxypeptidase enzyme produced by actinomadura R39, said incubation being conducted under conditions allowing the β-lactam antibiotic, if present in the said biological liquid, to react with the said enzyme to form an inactive and substantially irreversible equimolecular enzyme-antibiotic complex;
   (2) incubating the mixture obtained at the end of step (1) with a substrate solution under conditions allowing the substrate to be hydrolyzed by the said enzyme to form a compound in an amount proportional to the residual enzymatic activity;
   (3) determining the amount of the compound formed in step (2); and
   (4) comparing the value determined in step (3) with a standard to obtain the concentration of the β-lactam antibiotic in the biological liquid, the improvement which comprises incubating, in step (2), the mixture obtained at the end of step (1) with a solution of a substrate which is a thioester having the general formula $$R_1-R_2-S-CH(R_3)-COOH \quad (I)$$

wherein
$R_1$ represents a benzoyl, phenylacetyl or $N^\alpha$-acetyl-L-lysyl radical,
$R_2$ represents a glycyl or D-alanyl radical, and
$R_3$ is a hydrogen atom or a methyl radical,
which forms, by hydrolysis, a 2-mercaptoalkanoic acid having the formula:

$$HS-CH(R_3)-COOH \quad (II)$$

in which $R_3$ has the meaning given above, whereby said incubating is further conducted in the presence of a D-amino acid or of glycine, which activates the hydrolysis of the said substrate by the said enzyme.

2. The process of claim 1, wherein the substrate is [(N-benzoyl-D-alanyl)thio]-acetic acid.

3. The process of claim 1, wherein the D-amino acid is selected from group consisting of D-alanine, D-methionine, D-argine, D-phenylalanine, D-serine, D-histidine, D-valine, D-tryptophan and D-2-aminobutyric acid.

4. The process of claim 3, wherein the D-amino acid is D-alanine.

5. The process of claim 1, wherein steps (2) and (3) are conducted simultaneously.

6. The process of claim 1, wherein the β-lactam antibiotic to be determined is selected from the group consisting of benzylpenicillin, ampicillin, phenoxymethylpenicillin, carbenicillin, methicillin, oxacillin, cloxacillin, cephalosporin C, cephaloglycin, cephalothin, cephalexin and cephapirin.

7. The process of claim 1, wherein the amount of 2-mercaptoalkanoic acid having the formula (II) is determined by incubating the mixture obtained in step (2) with 5,5'-dithiobis(2-nitrobenzoic) acid to produce a coloration, the intensity of which is a function of the amount of 2-mercaptoalkanoic acid.

8. The process of claim 1, wherein said standard is a standard curve of β-lactam antibiotic concentration versus percentage residual enzymatic activity.

9. The process of claim 1, wherein the biological liquid is selected from the group consisting of milk, serum, saliva, meat extracts, fermentation liquids and buffered aqueous solutions.

10. The process of claim 1, wherein the biological liquid is selected from the group consisting of milk and serum.

11. A test set for the determination of a β-lactam antibiotic in a biological liquid, said set comprising:

(1) a definite amount of soluble D-alanyl-D-alaninecarboxypeptidase produced by Actinomadura R39;

(2) a definite amount of a substrate which is a thioester having the general formula $$R_1-R_2-S-CH(R_3)-COOH \quad (I)$$

wherein

R$_1$ represents a benzoyl, phenylacetyl or N$^\alpha$-acetyl-L-lysyl radical,

R$_2$ represents a glycyl or D-alanyl radical, and

R$_3$ is a hydrogen atom or a methyl radical, (3) a definite amount of a D-amino acid or of glycine, (4) a reagent allowing the determination of a 2-mercaptoalkanoic acid having the formula $$HS-CH(R_3)-COOH \quad (II)$$

in which R$_3$ has the meaning given above.

12. The test set of claim 11, wherein the substrate is [(N-benzoyl-D-alanyl)thio]-acetic acid.

13. The test set of claim 11, wherein the D-amino acid is selected from group consisting of D-alanine, D-methionine, D-arginine, D-phenylalanine, D-serine, D-histidine, D-valine, D-tryptophan and D-2-aminobutyric acid.

14. The test set of claim 13, wherein the D-amino acid is D-alanine.

15. The test set of claim 11, wherein reagent (4) is 5,5'-dithiobis(2-nitrobenzoic) acid.

16. The test set of claim 11, further comprising a standard with which the results of the tests carried out with reagents (1), (2), (3) and (4) may be compared.

17. The test set of claim 16, wherein said standard is a standard curve of β-lactam antibiotic concentration versus percentage residual enzymatic activity.

18. The test set of claim 11, wherein said substrate and reagent (4) are combined in the form of a tablet.

* * * * *